United States Patent [19]
Wright

[11] Patent Number: 5,254,773
[45] Date of Patent: Oct. 19, 1993

[54] PROCESS FOR PREPARING TELOMERS FROM ETHYLENE AND ALPHA, OMEGA-DIBROMOPERFLUOROALKYLALKANES IN THE PRESENCE OF ORGANIC FREE-RADICAL GENERATORS

[75] Inventor: Antony P. Wright, Rhodes, Mich.

[73] Assignee: Dow Corning Corporation, Midland, Mich.

[21] Appl. No.: 23,510

[22] Filed: Feb. 26, 1993

[51] Int. Cl.$^5$ .................. C07C 17/28; C07C 19/08
[52] U.S. Cl. .................................... 570/172; 570/139
[58] Field of Search ................................ 570/139, 172

[56] References Cited

U.S. PATENT DOCUMENTS

| | | | |
|---|---|---|---|
| 3,055,953 | 9/1962 | Smeltz | 260/653.1 |
| 4,058,573 | 11/1977 | Knell | 570/172 |
| 5,068,471 | 11/1991 | Paul et al. | 570/139 |

FOREIGN PATENT DOCUMENTS

| | | | |
|---|---|---|---|
| 576707 | 5/1959 | Canada | 570/139 |
| 470598 | 2/1992 | European Pat. Off. | |
| 685 | 11/1968 | Japan | 570/139 |

OTHER PUBLICATIONS

Aplied Polymer Symposium No. 22, 103-125 (1973) "High-Temperature Fluorosilicone Elastomers".
J. Fluorine Chem. I (1971/72), 203-218; "The Synthesis of Bis-(Silyl)Polyfluoroalkane Derivatives".
Ber. Bunsen-Ges. Phys. Chem., ; vol. 94 (No. 8), pp. 874-882; (1990); "Krypton Monofluoride . . . ".

Primary Examiner—Joseph E. Evans
Attorney, Agent, or Firm—Alexander Weitz

[57] ABSTRACT

A process is disclosed wherein a telomer having the formula $BrCH_2CH_2(CF_2CFX)_nCH_2CH_2Br$ is prepared by reacting a telogen of the formula $Br(CF_2CFX)_nCH_2CH_2Br$ with ethylene in the presence of an organic free-radical generator, wherein X is fluorine or a trifluoromethyl radical and n is an integer having a value of 1-5. It has been found that, when at least 0.05 mole of said free-radical generator is used for each mole of said telogen, the conversion of the telogen to the telomer is surprisingly increased.

18 Claims, 1 Drawing Sheet

PROCESS FOR PREPARING TELOMERS FROM ETHYLENE AND ALPHA, OMEGA-DIBROMOPERFLUOROALKYLALKANES IN THE PRESENCE OF ORGANIC FREE-RADICAL GENERATORS

FIELD OF THE INVENTION

The present invention relates to telomers of ethylene and alpha,omega-dibromoperfluoroalkylalkane telogens. More particularly, the invention is directed to an improved process for synthesizing specific industrially important telomers wherein at least 0.05 moles of an organic free-radical generator is added for each mole of alpha,omega-dibromoperfluoroalkylalkane telogen to be reacted with the ethylene.

BACKGROUND OF THE INVENTION

Fluorosilicone elastomers have long been known for their solvent resistance, flexibility at low temperatures and excellent high temperature properties. Many industrial and military applications have been developed which exploit these desirable characteristics (e.g., aircraft sealant in view of good resistance to jet fuel). A fluorosilicone-fluorocarbon hybrid system described by Pierce et al. (Applied Polymer Symposium, No. 22, 103-125, 1973) is stated to be particularly resistant to reversion at elevated temperatures, the repeat unit of such a hybrid polymer being exemplified by the formula $-RR\ SiCH_2CH_2CF_2CF_2CH_2CH_2SiRR'-$ wherein R is a methyl radical and R' is a trifluoropropyl radical. This hybrid polymer can be prepared by reacting a terminally unsaturated intermediate of the formula $CH_2=CHCF_2CF_2CH=CH_2$ with a chlorosilane of the formula $RR'SiHCl$ in the presence of a platinum catalyst, followed by hydrolysis and condensation of the resulting chlorine-terminated monomer. The terminally unsaturated intermediate, in turn, is prepared by the following series of steps:

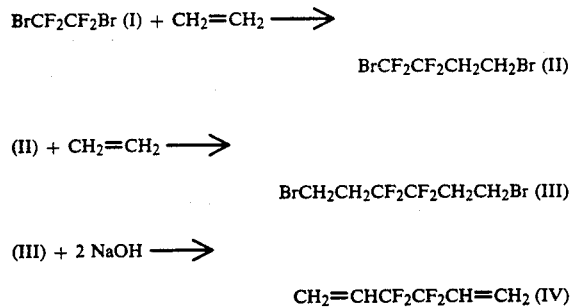

wherein the synthesis of dibromoperfluoroalkylalkanes (II) and (III) each takes place in the presence of a catalytic amount of an organic free-radical generator. Pierce et al, noted that, while the formation of compound (II) according to the first of these reactions is relatively facile, only "trace" amounts of the desired compound (III) result according to the second reaction wherein about 3 mole percent of an organic peroxide was used as the catalyst. This conclusion was also reported by Kim et al, in a previous paper (J. Fluorine Chem., 1, 203–218, 1971).

Although it is possible to produce small yields of telomer (III) directly from compound (I), this is not desirable. Under these conditions, it has been observed that a large excess of ethylene must be used and significant quantities of unwanted telomers of the type $BrCF_2CF_2(CH_2CH_2)_jBr$, in which j is an integer having a value of 2 to 10, are formed as byproducts. Therefore, the above describe sequence, wherein (I) is reacted with a deficiency of ethylene to form (II), the latter is isolated and subsequently further reacted with ethylene to form telomer (III), is the preferred route.

Reactions similar to those discussed by Pierce et al, and Kim et al., cited supra, are disclosed in U.S. Pat. No. 3,055,953 to Smeltz. Here, compounds of the type $Br(CH_2CH_2)_m(CF_2CF_2)_n(CH_2CH_2)_pBr$ and $Br(CF_2CF_2)_n(CH_2CH_2)_pBr$, in which m and p are integers in the range 1 to 6 and n is an integer in the range of 1 to 10, are prepared by reacting $Br(CF_2CF_2)_nBr$ or $Br(CF_2CF_2)_n(CH_2CH_2)_pBr$ with ethylene. These reactions are carried out at superatmospheric pressures at 50° C. to 200° C. in the presence of a free-radical generating catalyst. Starting pressures of at least 150 psi (1,034 kPa) are used and the molar ratio of peroxide catalyst to the bromofluorocarbon reactant was no greater than 0.043 in any of the examples. Example 5 of the Smeltz patent explicitly discloses the high pressure reaction of $Br(CF_2CF_2)_2CH_2CH_2Br$ with ethylene using a catalytic amount of t-butyl peroxide (i.e., peroxide/dibromide reactant in a molar ratio of 0.02/0.46=0.043. However, this reference does not specifically teach the corresponding reaction of $BrCF_2CF_2CH_2CH_2Br$ (II) with ethylene to produce the highly desirable product $BrCH_2CH_2CF_2CF_2CH_2CH_2Br$ (III).

Although the above references suggest that compounds of the type $BrCH_2CH_2CF_2CF_2CH_2CH_2Br$ can be prepared by the free-radical catalyzed telomerization of ethylene with a telogen of the type $BrCF_2CF_2CH_2CH_2Br$, the yield of the desired telomer product is relatively small, and these reactions are therefore more of academic than practical interest. Moreover, when the present inventor employed the methods of Kim et al. to react $BrCF_2CF_2CH_2CH_2Br$ with ethylene in the presence of t-butyl peroxide, the conversion of the telogen and yield of $BrCH_2CH_2CF_2CF_2CH_2CH_2Br$ were even lower than the corresponding values reported by Kim et al. It is believed that these lower values can be attributed, at least in part, to a more careful workup (i.e., distillation, analysis and material balance) of the reaction product mixture than was undertaken by Kim et al. There is therefore still a need for an improved process for synthesizing the highly desirable telomers described supra.

SUMMARY OF THE INVENTION

It has now been discovered that the conversion of telogens of the type illustrated above to the corresponding ethylene telomer can be significantly increased beyond the teachings of the above prior art. Contrary to these teachings, wherein a free-radical generator is merely considered a catalyst for the telomerization reaction, it has now been surprisingly found that this "catalyst" apparently partakes in the reaction, although its stoichiometry is yet to be elucidated. Also contrary to the teachings of the prior art, it has been discovered that there is no need to conduct the telomerization reaction at high pressures. Indeed, as described infra, the telomerization reaction is actually more efficient at lower pressures and can even be carried out at atmospheric pressure.

The present invention therefore relates to a process for the preparation of a telomer having the formula $BrCH_2CH_2(CF_2CFX)_nCH_2CH_2Br$ by reacting a telogen of the formula $Br(CF_2CFX)_nCH_2CH_2Br$ with ethylene in the presence of an organic free-radical generator, wherein X is independently selected from the group consisting of a fluorine radical and a trifluoromethyl radical and n is an integer having a value of 1-5, inclusive, wherein at least 0.05 mole of said free-radical generator is used for each mole of said telogen present. Although a strict definition of a telomer would require the value of n to be at least two, those skilled in the art should not be confused by the the terms "telogen" and "telomer"0 as used herein.

DETAILED DESCRIPTION OF THE INVENTION

Figure 1:
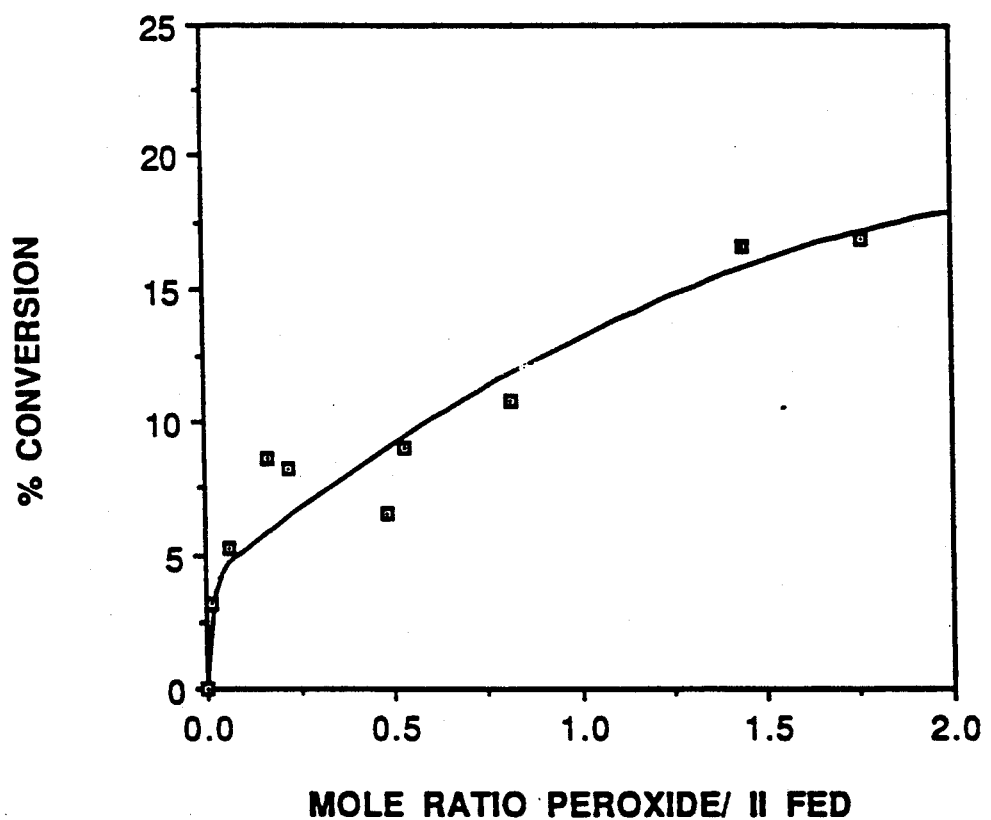
FIG. 1 is a plot of percent conversion of a telogen having the formula $Br(CF_2CF_2)CH_2CH_2Br$ to a telomer having the formula $BrCH_2CH_2(CF_2CF_2)CH_2CH_2Br$ as a function of the molar ratio of t-butyl peroxide to the telogen charged to a flow reactor.

In the telomerization process of the present invention, a telogen of the formula $Br(CF_2CFX)_nCH_2CH_2Br$, in which X is independently selected from the group consisting of a fluorine radical and a trifluoromethyl radical and n is an integer having a value of 1-5 inclusive, is reacted with ethylene and at least 0.05 moles of an organic free-radical generator for each mole of said telogen. The desired telomer product of this process has the structure $BrCH_2CH_2(CF_2CFX)_nCH_2CH_2Br$, in which X and n have their previously defined meanings. Although the value of n in the above formulae can be greater then about 5, these telomers are not readily distilled and are therefore of little commercial value. Additionally, it is preferred that n is no more than 3 when the telomer is to be employed in the above described preparation of fluorosilicone elastomers. When n is more than 3 the resultant fluorosilicon polymers generally have too high a glass transition temperature and tend to be more plastic than elastomeric in nature. Most preferably, $n=1$.

The group X in the above formulae representing the telogens and telomers of the present invention can be fluorine or a trifluoromethyl radical (i.e., $-CF_3$). Again, for the purposes of preparing the above described fluorosilicone elastomers, it is preferred that X is F. Thus, the most preferred telogen of the invention has the structure $BrCF_2CF_2CH_2CH_2Br$ and the associated telomer product has the structure $BrCH_2CH_2CF_2CF_2CH_2CH_2Br$, these compounds also being denoted herein by the Roman numerals (II) and (III), respectively.

The type of organic free-radical generator used in the process of the present invention is not specifically limited. This component may be selected from any of the known azo or diazo compounds, such as 2,2 azobisisobutyronitrile. Preferably, the free-radical generator is selected from organic peroxides such as hydroperoxides, diacyl peroxides, ketone peroxides, peroxyesters, dialkyl peroxides, peroxydicarbonates, peroxyketals, peroxy acids, acyl alkylsulfonyl peroxides and alkyl monoperoxydicarbonates.

It is further preferred that the free-radical generator have a 10-hour half life temperature within the approximate range 100° C. to 160° C. However, free-radical generators having a 10-hour half life temperature below about 100° C. may still be used provided that they are slowly and continuously introduced to the reaction mixture. It has been found that, when the telomerization reaction is carried out below about 100° C. the telogen $Br(CF_2CFX)_nCH_2CH_2Br$ tends to add multiple ethylene units to yield telomers of the general formula $Br(CH_2CH_2)_j(CF_2CFX)_n(CH_2CH_2)Br$, in which j is an integer having a value of 2 or more. On the other hand, when the reaction temperature is above about 160° C. there is an increasing tendency toward side reactions and the formation of undesirable residues.

Specific examples of suitable peroxides which may be used according to the process of the present invention include benzoyl peroxide, t-butyl peroxy O-toluate, cyclic peroxyketal, t-butyl hydroperoxide, t-butyl peroxypivalate, lauroyl peroxide and t-amyl peroxy 2-ethylhexanoate, inter alia. Examples of organic peroxides which fall into the above defined 10-hour half life temperature range include such compounds as di-t-butyl peroxide, 1,3-bis(t-butylperoxyisopropyl) benzene, 2,2,4-trimethylpentyl-2-hydroperoxide, 2,5-bis(t-butylperoxy)-2,5-dimethylhexyne-3, cumyl hydroperoxide, t-butyl peroxybenzoate and diisopropylbenzene mono hydroperoxide, inter alia. For the purposes of the process of the invention, it is preferred that the peroxide is di-tert-butyl peroxide (also referred to as t-butyl peroxide herein).

In order to practice the process of the present invention the above described telogen of the general formula $Br(CF_2CFX)_nCH_2CH_2Br$ is reacted with ethylene and a free-radical generator such that at least 0.05 mole of the free-radical generator is added for each mole of the telogen used, said reaction being carried out in the liquid state. As previously mentioned, the conversion of the telogen to the telomer is surprisingly increased as the amount of the free-radical generator is increased. Although no particular upper limit on the amount of free-radical generator has been observed, practical considerations would limit the level of this component. Thus, for example, a molar ratio of the free-radical generator to the telogen of much greater than about two would generally not be advisable based on process throughput efficiency, as well as safety, considerations. Preferably, about 0.06 to about 1.8 mole, and most preferably about 0.1 to 0.2 mole, of the peroxide free-radical generator is employed for each mole of the telogen.

The temperature at which the instant process is run depends upon the particular free-radical generator selected, but is preferably within the above stated preferred range. The duration of the telomerization reaction is, of course, a function of reaction temperature, a total time of at least one half life of the free-radical generator under these conditions generally being sufficient if the unreacted free-radical generator can be recovered and recycled. It is preferred that the ethylene partial pressure during the telomerization reaction is below approximately seven atmospheres (absolute pressure), most preferably in the range of about 1 to 2 atmospheres. It has been observed that the conversion of the telogen to the telomer, and the yield of the telomer, generally decline as the partial pressure is raised beyond the above mentioned range. Moreover, as the ethylene partial pressure is reduced, the amounts of byproducts such as $Br(CH_2CH_2)_2(CF_2CFX)_n(CH_2CH_2)Br$, as well as non-volatile residue, drops relative to desired telomer product. As used herein, the percent conversion of telogen to telomer is defined as:

(moles of telomer formed/moles of telogen supplied)×100; the percent yield of telomer is defined as:

(moles of telomer formed/moles of telogen consumed)×100.

The telomerization reaction can be carried out in either batch or continuous fashion, the following general processes types being illustrative:

Process A—A tube or autoclave is charged with all ingredients, sealed and heated. In this design, the pressure is determined by the amounts of ethylene and telogen charged. The use of large amounts of reactants leads to undesirably high pressures. Additionally, this could result in a dangerous exothermic reaction and this process type is therefore not preferred.

Process B—Same as above described Process A with the exception that the ethylene is continuously introduced at a rate sufficient to maintain the pressure in the autoclave at a preset level, but no material exits the system during the course of the reaction. Since the byproducts of decomposition of the free-radical generator are generally volatile, they contribute to the total pressure and therefore limit the amount of ethylene which can be introduced.

Process C—Same as above Process B with the exception that the ethylene is fed at a constant mass rate and the free-radical generator may be present initially or metered to the system at a controlled rate. As in Process B, no material exits the system during the course of the reaction.

Process D—Ethylene and the free-radical generator are fed at a constant rate to the bottom of a reactor initially charged with the telogen. The temperature at the top of the reactor can be independently controlled so as to reflux reactants back into the reactor while allowing byproducts to escape through an exit port. This exit port, also located at the top of the reactor, can be used to provide a constant back-pressure to the system.

Process E—Same as above Process D with the exception that the free-radical generator and the telogen are both charged to the reactor initially and the ethylene is introduced at a constant rate to the bottom of the reactor.

For the purposes of the present invention, it is preferred to employ a flow-through process such as Process D or Process E, particularly the latter, at a pressure in the range of about one to two atmospheres. For optimum conversion, the unreacted telogen may be recycled. Likewise, unreacted free-radical generator can also be recycled.

EXAMPLES

The following examples are presented to further illustrate the process of this invention, but are not to be construed as limiting the invention, which is delineated in the appended claims. All parts and percentages in the examples are on a weight basis and the pressure measurements are reported in terms of gage pressures above atmospheric pressure (e.g., psig), unless indicated to the contrary.

In addition, an abbreviated notation has been used to represent the fluorocarbons having the following formulae:

$BrCF_2CF_2Br=$ (I)

$BrCF_2CF_2CH_2CH_2Br=$ (II)

$BrCH_2CH_2CF_2CF_2CH_2CH_2Br=$ (III)

In the following examples products were identified by capillary gas-liquid chromatography (GLC) using 25 meter×0.2mm glass column and a flame ionization detector (FID). Oven temperature was programed at 40° C. for 5 minutes followed by heating at 10° C. per minute to 270° C. Peaks were identified by gas-liquid chromatography (GLC)/Mass Spectroscopy (MS). Major products were isolated by distillation or preparative GLC and identities confirmed by exact mass determinations and $^{19}F$ and $^1H$ nuclear magnetic resonance (NMR) studies. FID area percents were converted to weight percents using response factors previously determined by injecting known weight ratios of pure components into the GLC instrument.

EXAMPLE 1

In a typical synthesis of compound II from I, a Hastalloy ™ "C" autoclave was charged with 2,556 g (9.8 moles) of compound I. The compound I used was 96.7% pure (acetone and t-butyl alcohol impurities) and was recycled from a previous similar preparation of compound II. A small amount of ethylene was then used to purge the autoclave at atmospheric pressure. The autoclave was heated to 135° C. and the heat turned off. As the temperature started to drop, t-butyl peroxide (16.4g: 0.11 mol) was added rapidly, and then a continuous flow of ethylene was introduced to the bottom of the autoclave through a dip tube. The ethylene flow rate was controlled with a needle valve such that a flow of 2 liter/min was obtained when the flow was diverted to discharge at atmospheric pressure. A resulting exotherm again brought the temperature to 140° C. whereupon cooling water was applied to reduce the autoclave temperature to 134° C. Ten such cycles between 134° and 140° C. were carried out over a 30 minute period. After 60 minutes from the start of ethylene flow the pressure in the autoclave rose to 146 psi (1.007 kPa) and the reaction was terminated by closing the ethylene flow and cooling to room temperature.

The product (2.637 g) was removed via the dip tube from the unopened autoclave. FID GLC analysis indicated that this product consisted essentially of compound I (42.15 Area%), compound II 44.91 area, and minor impurity peaks. This product was distilled to recover 99.99% pure II. A material balance calculation indicated a 28% conversion and 80% yield of compound II based on the amount of compound I consumed.

EXAMPLE 2

Synthesis of compound III in a closed autoclave using slow ethylene feed (Process C was carried out as follows. A two-liter Hastalloy ™ autoclave was equipped with a stirrer, thermocouple wells, an electronic pressure transducer, a 3,000 psi (20,684 kPa) bursting disk, heating jacket and water cooling coils. The latter coils were activated to cool the system when the reaction temperature was ≧139° C. Compound II (as prepared in Example 1) (327 g, 98% pure; 1.113 mol) was charged to the autoclave. The system was cooled to 0° C. evacuated to an absolute pressure of 0.2 torr (27

Pa) and then purged with ethylene three times to remove oxygen. The autoclave was heated to 135° C. and 5 g of t-butyl peroxide was initially introduced, and then fed at a rate of 1.92 g/hr. using a high pressure metering pump. Ethylene gas was then fed continuously through a dip tube beneath the liquid surface. The ethylene was supplied at a pressure of 400 psi (2.758 kPa) and was fed to the autoclave through a needle valve which was adjusted to give a flow rate of 10 cc/min when the flow was diverted to discharge at atmospheric pressure. After six hours, the total pressure was 40 psi (276 kPa). After 13.5 hours, the peroxide feed was cut off and the reaction was continued for a total of 20 hours, at which point the total pressure was 114 psig (786 kPa). the total peroxide introduced being 37.3 g (0.2555 mole). Thus, a total of 0.22 mole of peroxide was used for each mole of compound II charged. The ethylene flow was then cut off and the system cooled, whereupon the pressure dropped to 38 psi (262 kPa) at 38° C.

At the conclusion of the reaction the autoclave contained a total of 362 g of a liquid mixture. This mixture was worked up by stripping and fractional vacuum distillation to isolate 37.0 g of 79.3% pure III. This product was further purified by recrystalization wherein it was mixed with iso-octane and cooled to −78° C. to provide a precipitate of 96% pure compound III having a melting point of 58° C. after being dried under vacuum. GLC analysis of the distillates in conjunction with an overall material balance calculation indicated that the product contained 200.3 g of unreacted II (0.703 mole), 29.5 g of product III (0.0933 mole), 40.8 g of residue, 58.3 g of low boilers consisting essentially of acetone and t-butyl alcohol, trace amounts of the compounds $BrCH_2CH_2CF_2CF_2CH_2CH_3$, $BrCH_2CH_2CF_2CF_2CH_2CH_2CH_2CH_2Br$ and unreacted peroxide. From the material balance and the known quantity of compound II charged to the reactor, the conversion of II to III and yield of this reaction were:

Conversion = $100 \times 0.0933/1.113 = 8.4\%$
Yield = $100 \times 0.942/(1.113−0.703) = 22.8\%$

EXAMPLE 3

The following example illustrates the synthesis of compound III in a flow reactor using a metered peroxide and ethylene feed (Process D).

A stainless steel pressure cylinder (300 cc capacity) was equipped with a heating jacket and an ⅛ in (3.2 mm) diameter dip tube positioned near its bottom for the introduction of reactants. A tube leading from an outlet port situated at the top of the cylinder was connected to a cold trap (−78° C.) which was fitted with a compressed air source to provide a back pressure of 10 psi (69 kPa). The cylinder was charged with 350.4 g (1.217 moles) of compound II and heated to a temperature of 140° C. and controlled at this set point. Feeds of ethylene gas and liquid t-butyl peroxide were combined and delivered to the cylinder through the dip tube. The ethylene flow rate was set at 22 cc/min (calibrated at atmospheric pressure). The peroxide was fed from a calibrated metering pump at a rate of 4.0 g/hr. During this run, the exit port and tubing above the reactor cylinder were separately maintained at a temperature of 45° C.

Reaction was carried out for 7.8 hours, at which point a total of 29.7 g (0.203 mole) t-butyl peroxide and 0.46 mole of ethylene had been fed to the cylinder. Thus, a total of 0.17 mole of peroxide was used for each mole of compound II.

At the conclusion of the reaction the cylinder contained a total of 334.4 g of a liquid mixture and the cold trap contained an additional 20.6 g of liquid. The contents of the cylinder were worked up by stripping and fractional vacuum distillation to isolate 39.1 g of 81.0% pure III. Analysis of the distillates, and cold trap contents, in conjunction with an overall material balance calculation, indicated that the product contained 23.4 g low boilers (mostly the byproducts t-butyl alcohol and acetone). 2.4 g of unreacted peroxide (0.0165 mole), 259.0 g of unreacted II (0.8992 mole), 32.9 g of product III (0.1041 mole), 26.6 g of residue and trace amounts of the compounds $BrCH_2CH_2CF_2CF_2CH_2CH_3$ and $BrCH_2CH_2CF_2CF_2CH_2CH_2CH_2CH_2Br$. From the material balance and the known quantity of compound II charged to the reactor, the conversion and yield of this reaction were:

Conversion = $100 \times 0.1041/1.217 = 8.6\%$
Yield = $100 \times 0.1052/(1.229−0.9089) = 32.9\%$

EXAMPLES 4–11

Synthesis of compound III according to the procedure of Example 3 was repeated wherein the molar ratio of the peroxide to the compound II introduced was varied between 0.01 and 1.76. In each case, the reaction pressure was held at 10 psi (69 kPa) the temperature was 137°–140° C. and the reaction time was 10–26 hours. Table 1 presents a summary of these parameters for each experiment, along with the respective conversion of II to III and the yield of the latter material.

TABLE 1

| Example | Reactor Temp. (°C.) | Reaction Time (hr) | Mole Ratio Peroxide/II | Conversion (%) | Yield (%) |
|---|---|---|---|---|---|
| 4* | 137 | 26 | 0.49 | 6.5 | 39.3 |
| 5* | 140 | 20 | 1.76 | 16.9 | 23.0 |
| 6* | 140 | 24 | 1.44 | 16.6 | 33.4 |
| 7* | 140 | 24 | 0.82 | 10.8 | 31.6 |
| 8 | 140 | 20 | 0.54 | 9.0 | 17.9 |
| 9 | 140 | 10 | 0.17 | 8.6 | 30.2 |
| 10 | 140 | 14 | 0.06 | 5.3 | 27.8 |
| 11 | 140 | 16 | 0.01 | 3.2 | 21.8 |

*approximately 1/20th scale runs; calculated values believed to be less accurate than those for full-scale runs.

The % conversion from Table 1 is plotted as a function of the peroxide mole ratio in FIG. 1, the plot being forced through the theoretical (0, 0) point. From this figure and Table 1 it can be seen that there is a drastic drop off in the conversion of compound II to compound III when the molar ratio of peroxide to compound II charged falls below about 0.05. Since the half-life of the t-butyl peroxide at the above reaction temperatures is less than about one hour, the variation of reaction time should have no impact after approximately four hours.

Synthesis of compound III according to the procedure of Example 9 was repeated wherein the molar ratio of the peroxide to the compound II introduced was 0.18, the temperature was 140° C. the reaction time was 18 hours and the pressure was 100 psi (689 kPa). The conversion of II to III was 6.0% and the yield was 19.6%. It can be seen that, even though this reaction was carried out for a longer time than that of Example 9, the effect of increased pressure resulted in diminished conversion and yield.

EXAMPLE 13

The following example illustrates the synthesis of compound III in a flow reactor using a metered ethylene feed wherein all the peroxide is initially present (Process E).

The reactor cylinder used in Example 3 was charged with 352.3 g of compound II (1.223 moles) and 30.5 g (0.211 mole) of liquid t-butyl peroxide. The reactor temperature was set at 113° C. and ethylene gas was fed beneath the liquid surface through the dip tube at a flow rate of 17 cc/min. The exit port and tubing above the reactor were heated separately at 45° C. and were connected to a cold trap held at −78° C. and under a back pressure of 10 psi (69 kPa). After 22 hours the temperature was raised to 125° C. and then slowly to 140° C. At this point, 25 hours had elapsed and a total of 1.1 moles of ethylene had been introduced; the run was terminated. In this example, a total of 0.17 mole of peroxide was used for each mole of compound II.

At the conclusion of the reaction the cylinder contained a total of 351.2 g of a liquid mixture and the cold trap contained no additional liquid. The contents of the cylinder were worked up by stripping and fractional vacuum distillation to isolate 48.3 g of 83.7% pure III. Analysis of the distillates, in conjunction with an overall material balance calculation, indicated that the product contained the byproducts t-butyl alcohol and acetone, 0.4 g of unreacted peroxide, 241.3 g of unreacted II (0.8377 mole), 40.4 g of product 111 (0.1278 mole), 38.1 g of residue and trace amounts of the compounds $BrCH_2CH_2CF_2CF_2CH_2CH_3$ and $BrCH_2CH_2CF_2CF_2CH_2CH_2CH_2CH_2Br$. From the material balance and the known quantity of compound II charged to the reactor, the conversion and yield of this reaction were:

Conversion = 100 × 0.1278/1.223 = 10.5%
Yield = 100 × 0.1278/(1.223−0.8377) = 33.2%

EXAMPLES 14–17

Synthesis of compound III according to the procedure of Example 13 was repeated under the conditions shown in Table 2 and at a pressure of 10 psi (689 kPa). The calculated conversion and yield are also presented for each experiment.

TABLE 2

| Example | Reactor Conditions (°C.) | (hr) | Mole Ratio Peroxide/II | Conversion (%) | Yield (%) |
|---|---|---|---|---|---|
| 14 | 113 | 22 | 0.17 | 9.6 | 35.7 |
| 15* | 113–126 | 25 | 0.17 | 9.0 | 33.6 |
| 16* | 113–140 | 40 | 0.18 | 10.8 | 35.3 |
| 17* | 113–140 | 41 | 0.18 | 11.8 | 38.1 |

*scaled up approximately ten fold in a one-gallon (≈4 liter) reactor.

EXAMPLE 18

The following example illustrates the preparation of compound III at atmospheric pressure in a flow reactor (Process E).

A 500 ml three-necked flask equipped with a sintered, stainless steel dispersion tube and a thermometer was charged with 350.6 g (1.211 mole) of compound II (99.5% pure) and 31.5 g (0.216 mole) of t-butyl peroxide. The flask was fitted with a 3 cm diameter × 35 cm long Vigreux distillation column which was topped by a distillation head and a reflux condenser. The distillation head was connected to a dry ice trap in series with an oil-filled bubble tube and then vented to the atmosphere. After purging the flask with ethylene to remove oxygen, heat was applied so as to control the temperature of the reaction at 116° C. Ethylene gas from a feed cylinder was then introduced beneath the surface of the above mentioned liquid reactants through the dispersion tube at a rate of 22 cc/min. In addition, ethylene was recirculated from the top of the reflux condenser back to the dispersion tube by means of a bellows pump at a rate of 104 cc/min. Thus, the total ethylene flow through the dispersion tube was at 126 cc/min. After 1.5 hours the ethylene flow from the feed cylinder was reduced to 12 cc/min. After 24.5 hours the temperature was raised to 124° C. and allowed to increase such that the contents reached 135° C. after 48 hours, at which point a total of 1.5 moles of ethylene had been introduced and the reaction was terminated. In this example, a total of 0.18 mole of peroxide was used for each mole of compound II.

The flask contained a total of 342 g of a liquid mixture and the cold trap contained 16 g of additional liquid. These liquids were worked up as before. Analysis and an overall material balance calculation indicated that the liquids contained 15.8 g of a mixture of the by-products t-butyl alcohol and acetone, 2.3 g of unreacted peroxidaa 226 g of unreacted II (0.785 mole), 44.8 g of product III (0.142 mole), 34.5 g of residue and trace amounts of the compounds $BrCH_2CH_2CF_2CF_2CH_2CH_2$ and $BrCH_2CH_2CF_2CF_2CH_2CH_2CH_2CH_2Br$. The conversion and yield of this reaction were:

Conversion = 100 × 0.142/1.211 = 11.7%
Yield = 100 × 0.142/(1.211−0.785) = 34.2%

EXAMPLE 19

The following example illustrates the synthesis of compound III in a flow reactor using a metered ethylene feed wherein all the peroxide was present initially (Process E) and the pressure was maintained at 115 psi (793 kPa).

A 600 cc Hastalloy, ™ "C" autoclave was fitted with a stirrer, thermocouple, electronic pressure transducer, a bursting disk, a heating jacket, water cooling coil and an inlet dip tube. The dip tube of the autoclave was connected to a metered ethylene gas supply. An exit stream from the autoclave was also metered and connected to a cold trap such that gasses could be vented at a controlled rate.

The autoclave was charged with 351.0 g of compound II (1.219 moles, 99.9% purity) and 30.9 g (0.211 mole) of liquid t-butyl peroxide. Nitrogen gas (100 cc/min) was fed through the dip tube for 20 minutes with the exit metering valve open and the temperature set at 25° C. to purge the system of oxygen. After this purging step, the inlet and exit valves were closed and the autoclave was heated to 113° C. Ethylene was fed through the dip tube at a rate of ≦50 cc/min until the pressure in the autoclave was 115 psi (793 kPa). The gas exit piping above the reactor was heated separately to 45° C. The exit valve was opened so as to allow a flow of 20 cc/min of excess ethylene to pass through the cold trap, the latter being maintained at −78° C. After 21 hours, the temperature was slowly raised to 139° C. the run being terminated after a total of 26.7 hours had elapsed. A total of 2.4 moles of ethylene were fed and 0.17 mole of peroxide was used for each mole of compound II charged.

At the conclusion of the reaction, the autoclave contained a total of 395.4 g of a liquid mixture and the cold trap contained 4.5 g of low boilers which were mostly tert-butanol and acetone. The contents of the autoclave were worked up by stripping and fractional distillation to isolate 34.8 g of 81.6% pure III. Analysis of the distillates in conjunction with an overall material balance calculation indicated that the product contained the byproducts acetone and t-butyl alcohol, 4.4 g unreacted peroxide, 233.3 g of unreacted compound II (0.8099 mole), 28.6 g of product III (0.0905 mole), 56.3 g residue and trace amounts of $BrCH_2CH_2CF_2CF_2CH_2CH_3$ and $BrCH_2CH_2CF_2CF_2CH_2CH_2CH_2CH_2Br$. The calculated conversion and yield of this reaction were:

Conversion = 100 × 0.0905/1.219 = 7.4 %
Yield = 100 × 0.0905/(1.219−0.8099) = 22.1%

EXAMPLE 20

The following example illustrates the synthesis of compound III wherein ethylene is metered into a reactor but no stream exits the reactor (Process B).

The procedure of Example 19 was followed with the exception that the exit valve remained closed and, when the autoclave temperature reached 113° C. ethylene gas was fed through the dip tube so as to maintain a pressure of 115 psi (793 kPa) for a period of 21 hours.

At the conclusion of the reaction, the autoclave contained a total of 380.0 g of a liquid mixture which was stripped to isolate 305.3 g of a mixture containing 5.6 wt % of pure compound III. Analysis of the distillate in conjunction with an overall material balance calculation, indicated that the product contained the byproducts acetone and t-butyl alcohol, 19.0 g of unreacted peroxide, 247.2 g of unreacted compound II (0.8582 mole), 17.0 g of product III (0.0538 mole), 46.8 g residue and trace amounts of $BrCH_2CH_2CF_2CF_2CH_2CH_2$ and $BrCH_2CH_2CF_2CF_2CH_2CH_2CH_2CH_2Br$. The calculated conversion and yield of this reaction were:

Conversion = 100 × 0.0538/1.219 = 4.4%
Yield = 100 × 0.0538/(1.219−0.8582) = 14.9%

That which is claimed is:

1. In a process for the preparation of a telomer having the formula $BrCH_2CH_2(CF_2CFX)_nCH_2CH_2Br$ comprising reacting a telogen of the formula $Br(CF_2CFX)_nCH_2CH_2Br$ with ethylene in the presence of an organic free-radical generator, wherein X is independently selected from the group consisting of a fluorine radical and a trifluoromethyl radical and n is an integer having a value of 1–5, inclusive, the improvement comprising using at least 0.05 mole of said free-radical generator for each mole of said telogen.

2. The process according to claim 1, wherein said free-radical generator is an organic peroxide.

3. The process according to claim 2, wherein the value of n is 1 to 3, inclusive.

4. The process according to claim 3, wherein X is fluorine.

5. The process according to claim 4, wherein n is 1.

6. The process according to claim 5, wherein 0.06 to 1.8 moles of said organic peroxide is used for each mole of said telogen.

7. The process according to claim 6, wherein 0.1 to 0.2 mole of said organic peroxide is used for each mole of said telogen.

8. The process according to claim 7, wherein said organic peroxide is t-butyl peroxide.

9. The process according to claim 1, wherein the value of n is 1 to 3, inclusive.

10. The process according to claim 9, wherein X is fluorine.

11. The process according to claim 10, wherein n is 1.

12. The process according to claim 11, wherein 0.1 to 0.2 mole of said free-radical generator is used for each mole of said telogen.

13. The process according to claim 1, wherein said process is a flow-through process carried out at a pressure of 1 to 2 atmospheres.

14. The process according to claim 2, wherein said process is a flow-through process carried out at a pressure of 1 to 2 atmospheres.

15. The process according to claim 5, wherein said process is a flow-through process carried out at a pressure of 1 to 2 atmospheres.

16. The process according to claim 6, wherein said process is a flow-through process carried out at a pressure of 1 to 2 atmospheres.

17. The process according to claim 7, wherein said process is a flow-through process carried out at a pressure of 1 to 2 atmospheres.

18. The process according to claim 8, wherein said process is a flow-through process carried out at a pressure of 1 to 2 atmospheres.

* * * * *